(12) United States Patent
Fischer

(10) Patent No.: US 9,514,273 B2
(45) Date of Patent: *Dec. 6, 2016

(54) DETECTION DEVICE FOR DETECTING A BLOOD PICTURE PARAMETER

(75) Inventor: Georg Fischer, Nuremberg (DE)

(73) Assignees: eesy-id GmbH, Graefelfing (DE); Friedrich-Alexander-Universitaet Erlangen-Nuernberg, Erlangen (DE)

( * ) Notice: Subject to any disclaimer, the term of this patent is extended or adjusted under 35 U.S.C. 154(b) by 431 days.

This patent is subject to a terminal disclaimer.

(21) Appl. No.: 13/884,332

(22) PCT Filed: Oct. 28, 2011

(86) PCT No.: PCT/EP2011/069021

§ 371 (c)(1),
(2), (4) Date: Jul. 17, 2013

(87) PCT Pub. No.: WO2012/069279

PCT Pub. Date: May 31, 2012

(65) Prior Publication Data

US 2013/0297223 A1    Nov. 7, 2013

(30) Foreign Application Priority Data

Nov. 24, 2010  (EP) .................................... 10192469

(51) Int. Cl.
*A61B 5/145* (2006.01)
*A61B 5/05* (2006.01)
*A61B 5/00* (2006.01)
*G06F 19/26* (2011.01)

(52) U.S. Cl.
CPC .............. *G06F 19/26* (2013.01); *A61B 5/0507* (2013.01); *A61B 5/14532* (2013.01); *A61B 5/6824* (2013.01)

(58) Field of Classification Search
CPC  A61B 5/145; A61B 5/1455; A61B 5/14551; A61B 5/14532; A61B 5/05; A61B 5/0507; A61B 5/6824
USPC ....... 600/309, 310, 316, 322, 323, 326, 340, 600/407, 430
See application file for complete search history.

(56) References Cited

U.S. PATENT DOCUMENTS

2006/0025664 A1  2/2006  Kim et al.
2008/0319285 A1*  12/2008  Hancock ....................... 600/309
2009/0275814 A1  11/2009  Watanabe et al.

FOREIGN PATENT DOCUMENTS

KR   100910034000   7/2009
WO   WO-2007145143 A1  12/2007
WO   WO-2010131029 A1  11/2010

OTHER PUBLICATIONS

Office Action in KR Application No. 10-2013-7014041 dated Aug. 28, 2014.
International Search Report for PCT/EP2011/069021 dated Mar. 2, 2012.

* cited by examiner

*Primary Examiner* — Tse Chen
*Assistant Examiner* — Chu Chuan (JJ) Liu
(74) *Attorney, Agent, or Firm* — Marshall, Gerstein & Borun LLP

(57) ABSTRACT

A detection device for detecting a blood count parameter of a blood component in a blood vessel comprising a transmitter, a receiver, a loss detector, and a processor. The transmitter injects a first transmit signal into the blood vessel at a first frequency and a second transmit signal into the blood vessel at a second frequency. The receiver receives a first receive signal at the first frequency and a second receive signal at the second frequency. The loss detector determines a first loss value on the basis of the first transmit signal and the first receive signal, and determines a second loss value on the basis of the second transmit signal and the second receive signal. The processor determines a relaxation time constant of the blood component in accordance with the frequency having the greater loss value, and determines the blood count parameter in accordance with the determined relaxation time constant.

19 Claims, 24 Drawing Sheets

DETECTION DEVICE FOR DETECTING A BLOOD PICTURE PARAMETER

BACKGROUND OF THE INVENTION

1. Field of the Invention

The present invention relates to the field of detecting a concentration of a blood constituent, for example sugar in blood flowing through a blood vessel.

2. Related Technology

In order to ascertain a blood picture parameter, such as, for example, a concentration of a blood constituent, blood can be taken invasively. The blood picture parameter can then be ascertained using the taken blood by means of standardized test strips, the electric resistance values of which depend on the concentration of the blood constituent, e.g. blood sugar. By way of example, the respective electric resistance value can be detected using a blood sugar measuring instrument, which carries out a DC current resistance measurement for detecting an electric resistance value of a test strip. The resistance value can be converted into a blood sugar concentration on the basis of a relationship, known per se, between a blood sugar concentration and a resistance value. In order to obtain high detection accuracy, each test strip is provided with calibration data, for example with a reference resistance value or with a corresponding code, as a result of which variations of properties of the test strips can be compensated for. However, a disadvantage of invasive methods is the necessity of taking blood and hence of injuring a patient. Moreover, continuous detection of a concentration of a blood constituent, for example to establish the diurnal variation curve thereof, is complicated. Furthermore, it is not possible to detect a time delay between food being taken and, for example, an increase in the blood sugar accurately by means of the invasive method. Also, particularly in the case of a low concentration of the blood sugar in blood, the time for administering insulin to the patient cannot be ascertained accurately.

For noninvasive ascertaining of a blood picture parameter such as, for example, a substance concentration or a substance composition in the blood, use can be made of microwave-spectroscopic methods. Microwave spectroscopy for detecting blood picture parameters is based on coupling a microwave signal into tissue perfused by blood and detecting a frequency-dependent absorption of coupled-in microwave energy.

The article "Non-invasive glucose monitoring in patients with Type 1 diabetes: A multi-sensor system combining sensors for dielectric and optical characterization of skin", Biosensors and Bioelectronics 24 (2009) 2778-2784 by Andreas Caduff et al. describes a multi-electrode arrangement for microwave-based ascertaining of a blood picture parameter. The multi-electrode arrangement comprises a plurality of electrode pairs with different electrode spacings, by means of which different penetration depths of microwave signals can be realized. The blood picture parameter is detected by means of an impedance measurement, i.e. by means of a one-port measurement, and is therefore susceptible to errors in the case of possible impedance maladjustments. As a result of different penetration depths, it is sometimes not possible to distinguish between capillary and venous blood, which can falsify the measurement results. In general, a measurement of a blood picture parameter using venous blood is more precise than a measurement of the blood picture parameter using capillary blood because, for example, blood sugar changes in capillary blood are delayed compared to venous blood.

The articles "A microwave frequency sensor for non-invasive blood-glucose measurement", SAS 2008—IEEE Sensors Applications Symposium, Atlanta, Ga., Feb. 12-14, 2008, by Buford Randal Jean et al. and "Calibration methodology for a microwave non-invasive glucose sensor", Master's Thesis, Baylor University, May 2008 by M. McClung describe a further electrode arrangement for ascertaining a blood sugar concentration. What is exploited here is that the dielectric properties of blood depend on a blood sugar content. By pressing a thumb onto the microwave sensor, a change in the relative permittivity of the thumb is measured by a detuning of a resonator. However, blood is displaced by the contact pressure of the thumb, and this can lead to falsification of the measurement results. Moreover, the measurements cannot be carried out continuously. The evaluation of the measurement data for ascertaining the blood sugar content moreover depends on the respective patient and is therefore not reproducible in other patients. Moreover, this method does not allow control of the penetration depth of the microwave power, and so it is not possible to distinguish between capillary and venous blood. Furthermore, the change in the relative permittivity is carried out on the basis of a one-port measurement, which is susceptible in respect of maladjustments.

SUMMARY OF THE INVENTION

The invention provides an efficient concept for microwave-based, non-invasive ascertaining of a blood picture parameter, in particular of a concentration of blood sugar, in blood flowing through a blood vessel.

Accordingly, the invention provides a detection device for detecting a blood picture parameter of a blood constituent of blood in a blood vessel, comprising:

a transmitter, which is configured to couple a first transmission signal with a first frequency and a second transmission signal with a second frequency into the blood vessel;

a receiver, which is configured to receive a first reception signal at the first frequency and a second reception signal at the second frequency;

a loss detector, which is configured to:

establish a first loss variable on the basis of the first transmission signal and the first reception signal, and establish a second loss variable on the basis of the second transmission signal and the second reception signal; and a processor, which is configured to ascertain a relaxation time constant of the blood constituent depending on the frequency with the greater loss variable.

The invention further provides a method for detecting a blood picture parameter of a blood constituent of blood in a blood vessel, comprising the following steps:

coupling a first transmission signal with a first frequency and a second transmission signal with a second frequency into the blood vessel;

receiving a first reception signal at the first frequency and a second reception signal at the second frequency;

establishing a first loss variable on the basis of the first transmission signal and the first reception signal;

establishing a second loss variable on the basis of the second transmission signal and the second reception signal; and ascertaining a relaxation time constant of the blood constituent depending on the frequency with a greater loss variable.

The invention is based on the discovery that a blood picture parameter can be established by detecting a relaxation time constant of a blood constituent. By way of example, if the blood picture parameter to be ascertained is a concentration of blood sugar in the blood, a relaxation time constant of a water solution containing sugar is a measure for the concentration of the blood sugar, i.e. for the blood sugar level.

The invention is furthermore based on the discovery that the relaxation time constant of the blood constituent can be ascertained by measuring microwave signals coupled into the blood vessel. Here, loss variables of the coupled-in microwave signals are detected. By way of example, the loss variables are represented by the frequency-dependent profile of the complex relative permittivity.

The invention is based on the further discovery that a blood vessel such as, for example, a vein or an artery, the fatty tissue surrounding this blood vessel and the layer of skin situated thereover can be considered to be a dielectric waveguide system. Thus, if such a dielectric waveguide system is excited, it is possible to excite different modes or waves types, for example transverse electromagnetic (TEM) waves or transverse electric (TE) waves or transverse magnetic (TM) waves or an HE wave. In the case of a TE mode, there is a component of the magnetic field, different from zero, which points in the propagation direction. By contrast, in the case of a TM mode, there is a component of an electric field, different from zero, which points in the mode propagation direction. Thus, depending on a radiofrequency excitation, it is possible to excite different modes in a dielectric waveguide system, which comprises the blood vessel and the layer of skin, which modes can also propagate in the blood flow direction, as a result of which an accurate detection of a blood picture parameter is possible.

The blood vessel, into which the transmission signals are coupled-in and from which the reception signals are decoupled, is interpreted as a dielectric waveguide. The transmission signals are, in particular, embodied as microwave signals. As a result of using microwave signals, a robust measurement methodology is made possible.

It is possible to establish at least one blood picture parameter, e.g. the glucose concentration in the blood, by means of the ascertained relaxation time constant (τ). The blood picture parameter can—like the relaxation time constant (τ) of the blood constituent—be established continuously. By way of example, for the glucose concentration as a blood picture parameter, this results in an advantage compared to conventional solutions: it becomes possible to ascertain the delay time between food intake of the patient and the blood sugar increase. It follows that it is possible to react quicker to variations in the daily routine of the patient. An alarm can be triggered immediately if it becomes apparent that there is too much or too little sugar. A telemedical link via a communication interface is also possible.

By using the first transmission signal, the second transmission signal and, potentially, further transmission signals, a broadband measurement or establishment in respect of the loss variables is possible.

In accordance with one aspect of the invention, a detection device for detecting a blood picture parameter of a blood constituent of blood in a blood vessel is proposed, which detection device comprises a transmitter, a receiver, a loss detector and a processor. The transmitter is configured to couple a first transmission signal with a first frequency and a second transmission signal with a second frequency into the blood vessel. The receiver is configured to receive a first reception signal at the first frequency and a second reception signal at the second frequency. The loss detector is configured to establish a first loss variable on the basis of the first transmission signal and the first reception signal. The loss detector is furthermore configured to establish a second loss variable on the basis of the second transmission signal and the second reception signal. The processor is configured to ascertain a relaxation time constant (τ) of the blood constituent depending on the frequency with the greater loss variable.

In particular, the processor is configured to ascertain the relaxation time constant (τ) of the blood constituent depending on the first frequency if the first loss variable is no smaller than the second loss variable, or to ascertain the relaxation time constant (τ) of the blood constituent depending on the second frequency if the second loss variable is no smaller than the first loss variable.

In accordance with one embodiment, the processor is configured to establish at least one blood picture parameter depending on the ascertained relaxation time constant (τ).

In accordance with one embodiment, the processor is configured to establish at least one blood picture parameter depending on the ascertained relaxation time constant (τ) by means of a predetermined relationship between the concentration of the blood picture parameter and the relaxation time constant (τ).

In accordance with one embodiment, the predetermined relationship comprises a map of the concentration of the blood picture parameter on the relaxation time constant (τ).

In accordance with one embodiment, the detection device comprises a look-up table, by means of which the predetermined relationship between the concentration of the blood picture parameter and the relaxation time constant (τ) is mapped.

In accordance with one embodiment, the at least one blood picture parameter comprises a glucose concentration in the blood, a lactate concentration in the blood or an oxygen concentration in the blood.

In accordance with one embodiment, the loss detector is configured to ascertain the first loss variable and the second loss variable by means of a two-port measurement.

Advantageously, the two-port measurement provides a more reliable measurement result than a conventional one-port measurement.

In accordance with one embodiment, the loss detector comprises a network analyzer or a power detector.

In accordance with one embodiment, the loss detector is configured to ascertain in each case a forward transmission factor $S_{21}$ and/or an input reflection factor $S_{11}$ in order to ascertain the first loss variable and the second loss variable.

In accordance with one embodiment, the loss detector is configured to ascertain in each case the first loss variable and the second loss variable on the basis of the following formula:

$P_{loss}=1-|S_{11}|^2-|S_{21}|^2$, where $P_{loss}$ denotes the respective loss variable, and where $S_{11}$ denotes the input reflection factor and $S_{21}$ denotes the forward transmission factor.

In accordance with one embodiment, the processor is configured to ascertain the relaxation time constant (τ) on the basis of the following formula:

$$\tau = \frac{1}{2\pi f_A}$$

where $f_A$ denotes the frequency at which the established loss variable is greater.

In accordance with one embodiment, the loss detector is configured to establish the complex relative permittivity (∈") at the respective frequency for ascertaining the respective loss variable.

In the process, it is, in particular, the imaginary part of the complex dielectric constant or relative permittivity which is evaluated. In particular, those frequencies are considered at which the imaginary part of the complex relative permittivity has a local maximum. As a result, it is possible to separate different polar effects by observing the imaginary part of the complex dielectric constant, which represent the frequency-dependent losses.

In accordance with one embodiment, the processor is configured to ascertain the frequency at which the imaginary part of the complex relative permittivity ($\in$") is at a maximum and to establish the relaxation time constant (T) depending on the ascertained frequency.

In accordance with one embodiment, the transmitter is configured to couple at least one transmission signal with a multiplicity of frequencies into the blood vessel. Here, the receiver is configured to receive at least one reception signal with the multiplicity of frequencies. Furthermore, the processor is configured to ascertain the frequency at which the complex relative permittivity ($\in$") is at a maximum and to establish the relaxation time constant (T) depending on the ascertained frequency.

In accordance with one embodiment, the transmitter for coupling-in the first transmission signal or the second transmission signal has at least one transmission antenna, in particular a dipole antenna, a frame antenna or a patch antenna. In accordance with this preferred embodiment, the receiver for receiving the first reception signal and the second reception signal has at least one reception antenna, in particular a dipole antenna or a frame antenna, which is at a distance from the transmission antenna.

In accordance with one embodiment, the transmitter is configured to couple the first transmission signal or the second transmission signal into the blood vessel as a transverse electric (TE) wave or as a transverse magnetic (TM) wave, in particular longitudinally or transversely with respect to a blood flow direction.

In accordance with one embodiment, the transmitter is configured to couple the first transmission signal and the second transmission signal into the blood vessel successively, in particular by means of a tunable oscillator, or simultaneously, in particular by means of a broadband signal comprising the first transmission signal and the second transmission signal.

In accordance with one embodiment, the transmission signal is a broad-edge radiofrequency signal or a sweep signal.

In accordance with one embodiment, the transmission signal is formed as a microwave signal.

In accordance with one embodiment, the blood vessel is an artery or a vein.

In accordance with one embodiment, the transmitter couples the transmission signal into the blood vessel with a power from 0.1 to 1.0 mW.

In accordance with one embodiment, the first frequency and the second frequency respectively lie in a frequency range between 1 GHz and 15 GHz.

In accordance with one embodiment, the detection device comprises a transmitter with a number of transmission antennas for emitting at least one transmission signal, a receiver with a number of reception antennas for receiving at least one reception signal, the processor and the loss detector. Here, the processor is configured to select a first detection configuration comprising one transmission antenna of the number of transmission antennas and one reception antenna of the number of reception antennas and to select a second detection configuration comprising one transmission antenna of the number of transmission antennas and one reception antenna of the number of reception antennas. Furthermore, the loss detector is configured, if the first detection configuration for emitting a transmission signal is selected, to detect a first loss variable on the basis of the transmission signal and a reception signal and, if the second detection configuration for emitting a transmission signal is selected, to detect a second loss variable on the basis of the transmission signal and a reception signal. Furthermore, the processor is configured to select the detection configuration with the smaller loss variable for detecting the blood picture parameter.

By way of example, the transmitter is formed as a transmitter with a broadband pseudo-noise signal, for example as an M-sequence radar.

In particular, if the first detection configuration is selected, the transmitter is configured to emit the transmission signal by means of the transmission antenna of the first detection configuration. If the first detection configuration is selected, the receiver is configured to receive the reception signal by means of the reception antenna of the first detection configuration. Furthermore, if the second detection configuration is selected, the transmitter is configured to emit the transmission signal by means of the transmission antenna of the second detection configuration, wherein, if the second detection configuration is selected, the receiver is configured to receive the reception signal by means of the reception antenna of the second detection configuration. Here, the loss detector is configured to detect the first loss variable on the basis of the transmission signal and the reception signal of the first detection configuration and to detect the second loss variable on the basis of the transmission signal and the reception signal of the second detection configuration.

In accordance with one embodiment, the first loss variable is an absorption line of a water solution with a blood constituent at the first frequency and the second loss variable is an absorption line of the water solution at the second frequency.

In accordance with one embodiment, the first loss variable and the second loss variable define a frequency-dependent profile of absorption lines of a water solution with the blood constituent.

In accordance with one embodiment, the first loss variable is an absorption minimum or an absorption maximum in a first frequency range comprising the first frequency, with the second loss variable being an absorption minimum or an absorption maximum in a second frequency range comprising the second frequency.

In accordance with one embodiment, the invention relates to a detection device for detecting a blood picture parameter of blood in a blood vessel, comprising a transmitter with a number of transmission antennas for emitting at least one transmission signal, a receiver with a number of reception antennas for receiving at least one reception signal, a processor, which is configured to select a first detection configuration comprising one transmission antenna of the number of transmission antennas and one reception antenna of the number of reception antennas and to select a second detection configuration comprising one transmission antenna of the number of transmission antennas and one reception antenna of the number of reception antennas, a loss detector, which is configured, if the first detection configuration for emitting a transmission signal is selected, to detect a first loss variable on the basis of the transmission signal and a reception signal and, if the second detection configuration for emitting a transmission signal is selected, to detect a second loss variable on the basis of the transmission signal and a reception signal, wherein the processor is configured to select the detection configuration with the smaller loss variable for detecting the blood picture parameter.

During the selection of the respective detection configuration, it is preferable for the blood vessel to be excited, wherein the transmission signals are, for example, emitted in the direction of the blood vessel. On the basis of the reception signals, which are received versions of the transmission signals, and on the basis of the transmission signals it is possible, for example, to select that antenna pair, comprising a transmission antenna and a reception antenna, as that detection configuration which is connected with the smallest coupling-in losses. The coupling-in losses can, for example, be detected on the basis of a comparison of the aforementioned loss variables, for example absorption lines or attenuations.

In accordance with one aspect of the invention, a method for detecting a parameter of a blood constituent of blood in a blood vessel is proposed. Here, a first transmission signal with a first frequency and a second transmission signal with a second frequency are coupled into the blood vessel. Furthermore, a first reception signal is received at the first frequency and a second reception signal is received at the second frequency. A first loss variable is established on the basis of the first transmission signal and the first reception signal. Accordingly, a second loss variable is established on the basis of the second transmission signal and the second reception signal. Furthermore, a relaxation time constant ($\tau$) of the blood constituent is established depending on the frequency with a greater loss variable.

In accordance with a preferred embodiment, the method comprises the following steps:

coupling at least one radiofrequency signal with a multiplicity of frequencies into the blood vessel, ascertaining the frequency at which the imaginary part of the complex relative permittivity ($\in$") is at a maximum, establishing the relaxation time constant ($\tau$) depending on the ascertained frequency, and establishing the blood picture parameter depending on the ascertained relaxation time constant ($\tau$).

Furthermore, a computer program product is proposed, which, on a program-controlled apparatus, prompts at least part of the method as described above for detecting a parameter of a blood constituent of blood in a blood vessel to be carried out. The at least one part, which is embodied as a computer program product, in particular comprises the step of establishing the relaxation time constant ($\tau$).

A computer program product such as a computer program means can, for example, be provided or supplied as a storage medium, such as a memory card, USB stick, floppy disk, CD-ROM, DVD or else in the form of a downloadable file from a server in a network. By way of example, in a wireless communication network, this can be brought about by the transmission of a corresponding file with the computer program product or the computer program means.

BRIEF DESCRIPTION OF THE DRAWINGS

Further exemplary embodiments will be explained with reference to the attached drawings. In detail:

FIG. 5 shows a schematic flowchart of a method for detecting a blood picture parameter of blood in a blood vessel;

DETAILED DESCRIPTION

Figure 1:
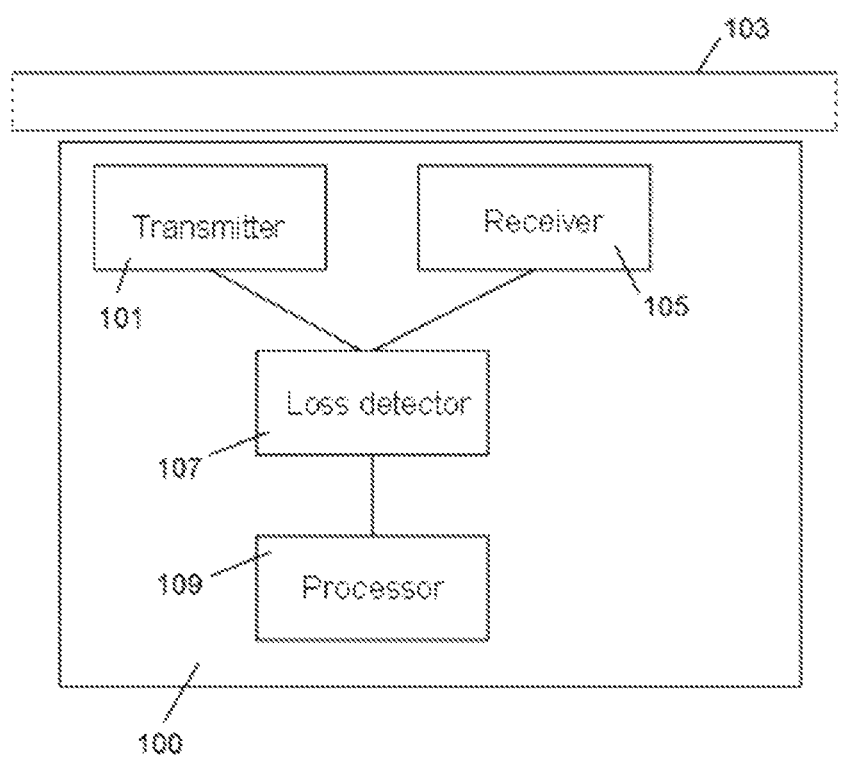
FIG. 1 shows a schematic block diagram of a detection device.

FIG. 1 shows a block diagram of a detection device 100 for detecting a blood picture parameter, such as, for example, a concentration of blood sugar or glucose. The detection device 100 comprises a transmitter 101, which is configured to couple a first transmission signal with a first frequency and a second transmission signal with a second frequency into the blood vessel 103 illustrated schematically in FIG. 1. The first transmission signal and the second transmission signal can, for example, together result in a broadband signal. The transmitter 101 can furthermore be configured to couple the first transmission signal and the second transmission signal, one after the other, into the blood vessel 103 in sequence. To this end, the transmitter 101 can have one or more transmission antennas, which, for example, are formed as dipole antennas.

The detection device 100 furthermore comprises a receiver 105, which is configured to receive a first reception signal at the first frequency and a second reception signal at the second frequency. To this end, the receiver 105 can have one or more reception antennas.

Furthermore, the detection device 100 has a loss detector 107, which is, for example, coupled to the transmitter 101 and the receiver 105 and provided for ascertaining a first loss variable on the basis of the first transmission signal and the first reception signal and also a second loss variable the basis of the second transmission signal and the second reception signal.

The detection device 100 furthermore has a processor 109, which is coupled to the loss detector 107 and provided for ascertaining a relaxation time constant τ of the blood picture parameter depending on the frequency with the greater loss variable.

By way of example, the processor 109 will ascertain the relaxation time constant of the blood picture parameter depending on the first frequency if the first loss variable is greater than the second loss variable. Correspondingly, the processor 109 will ascertain the relaxation time constant (τ) of the blood picture parameter depending on the second frequency if the second loss variable is greater than the first loss variable.

The detection device 100 illustrated in FIG. 1 uses the discovery that a blood vessel such as e.g. a vein, a layer of skin and fatty tissues surrounding a vein can be considered to be a dielectric waveguide. The makeup of a human forearm is described in Netter, F. N. "Atlas der Anatomie" [Anatomical Atlas], Thieme Verlag, 2006. Accordingly, a human forearm in cross-section consists of two bones which are surrounded by muscular tissue. Distributed around the muscular tissue are surface veins. The bones, the muscular tissue and the veins are encapsulated by fatty tissue, which is covered by upper layers of skin. The surface veins are arranged relatively close to the upper layers of skin and separated therefrom by the fatty tissue.

By way of example, if the transmitter 101 and the receiver 105, illustrated in FIG. 1, are placed onto the upper layer of skin, the transmitter 101 can be used to couple a transverse electric (TE) wave or a transverse magnetic (TM) wave into the dielectric waveguide system formed by a vein, fatty tissue and a layer of skin. Here, the layer of skin and the fatty tissue can be understood to be a thin-film waveguide.

As already explained above, the loss detector 107 is configured to establish a first loss variable on the basis of the first transmission signal and the first reception signal and to establish a second loss variable on the basis of the second transmission signal and the second reception signal. If use is made of further transmission signal and reception signal pairs, the loss detector 107 will accordingly establish further loss variables.

In particular, the loss detector 107 is configured to ascertain the loss variables by a two-port measurement. By way of example, the loss detector 107 comprises a network analyzer or a power detector.

Furthermore, the loss detector 107 is configured to ascertain in each case a forward transmission factor $S_{21}$ and an input reflection factor $S_{ii}$ in order to ascertain the loss variables.

Here, the loss detector will calculate the respective loss variable $P_{loss}$ by means of the following formula:

$$P_{loss} = 1 - |S_{11}|^2 - |S_{21}|^2.$$

In particular, the loss detector 107 is configured to establish the complex relative permittivity ∈" for ascertaining the respective loss variable.

Figure 2:
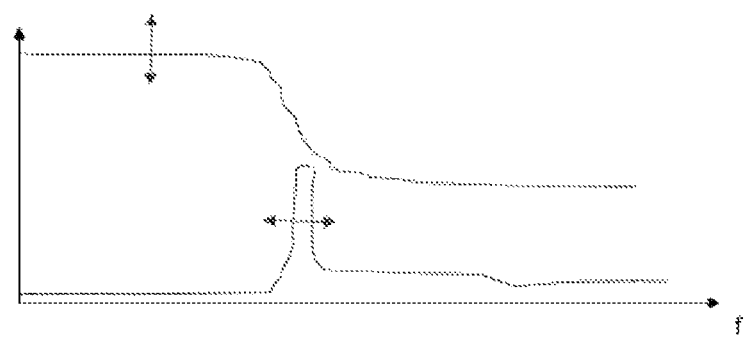
FIG. 2 shows a diagram for illustrating the real relative permittivity $\in$' and the complex relative permittivity $\in$" depending on the frequency.

To this end, FIG. 2 shows a diagram for illustrating the real relative permittivity ∈' and the complex relative permittivity ∈" depending on the frequency f.

Here, FIG. 2 illustrates that the losses represented by the complex relative permittivity ∈" increase in the frequency range where the real part ∈' transitions from the higher level to the lower level. This increase in the losses is also referred to as absorption lines in spectroscopy. The effect that can be used in this case is that the frequency at which the excesses of the losses—see local maximum of ∈"—is displaced with the concentration of the sugar content.

By way of example, the human body consists of 80% water. Water has absorption lines, for example at 19 GHz and 50 GHz. The detuning thereof can be ascertained and plotted against the sugar content. The detuning of the resonant frequency at ∈" is—as illustrated in FIG. 2—easier to detect than the change in the plateau of ∈'. In particular, variations in the coupling advantageously do not shift the frequency of the maximum of ∈". As a result, ascertaining the sugar concentration by observing ∈" is significantly less susceptible to errors than observing ∈' or the level change therein.

Since such curves as are superimposed in FIG. 2 in a multiplicity of substances, a separation of the substances by observing the imaginary relative permittivity ∈" is easier to carry out since each substance can be associated with a specific absorption maximum. However, in the case of the real relative permittivity ∈', it is only possible to observe the sum of all real relative permittivities ∈' of all substances involved.

As already explained above, the processor 109 is configured to ascertain the relaxation constant τ of the blood picture parameter depending on the frequency with the larger or maximum loss variable. Furthermore, the processor 109 is configured to establish the blood picture parameter, such as the glucose concentration in the blood, depending on the ascertained relaxation time constants.

Figure 3:
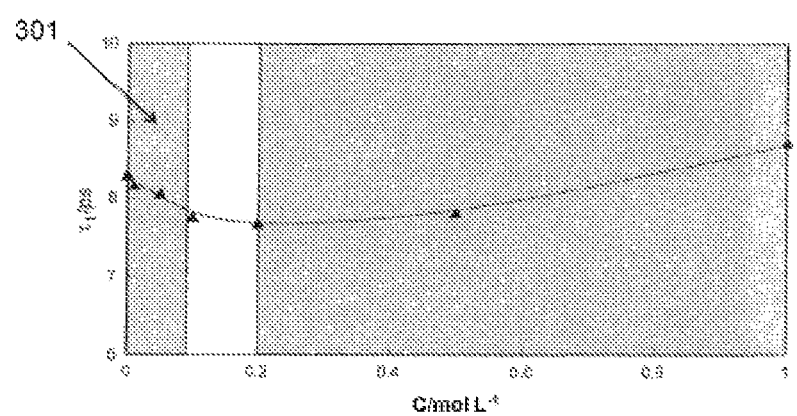
FIG. 3 shows a diagram for illustrating a relationship between the relaxation time constant ($\tau$) and the glucose concentration in the blood.

To this end, FIG. 3 shows a diagram for illustrating a relationship between the relaxation time constant (τ) and the glucose concentration C/mol L$^{-1}$ in the blood. Here, the area denoted by the reference sign 301 in FIG. 3 shows a critical blood sugar range.

Furthermore, the processor 109 is, in particular, configured to calculate the relaxation time constant (τ) on the basis of the formula $$\tau = \frac{1}{2\pi f_A},$$

where $f_A$ denotes the frequency at which the established loss variable is at a maximum.

Advantageously, the processor 109 is then configured to ascertain the frequency at which the imaginary part of the complex relative permittivity ∈" is at a maximum, and at which the relaxation time constant (τ) is to be established depending on the ascertained frequency. This ascertained frequency is then used by the processor 109 for ascertaining the blood picture parameter, such as the glucose concentration.

Figure 4:
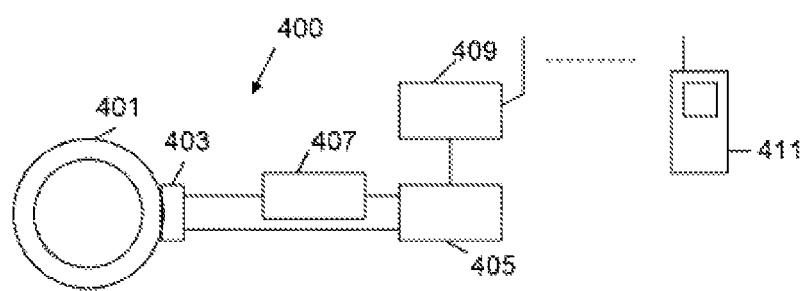
FIG. 4 shows a schematic block diagram of a detection device with a communication device.

FIG. 4 shows a schematic block diagram of a detection device 400. The detection device 400 has an armband 401, a sensor array 403 attached to the armband 401, a microprocessor 405, a microwave circuit 407 for generating the transmission signals, and a communication device 409.

By way of example, the sensor array 403 has a microwave sensor, a temperature sensor and a moisture sensor.

By way of example, the microprocessor 405 is configured like the processor 109 in FIG. 1.

The communication device 409 is configured for providing a communication link between the detection device 400 and a further communication device 411. By way of example, the communication device 409 comprises a Bluetooth interface. By way of example, the further communication device 411 is a mobile radio device, a smartphone or a GPS-based apparatus.

FIG. 5 illustrates a schematic flowchart of an exemplary embodiment of a method for detecting a blood picture parameter, such as, for example, a glucose concentration, of blood in a blood vessel.

In step 501, a first transmission signal with a first frequency and a second transmission signal with a second frequency are coupled into the blood vessel.

In step 503, a first reception signal is received at the first frequency and a second reception signal is received at the second frequency.

In step 505, a first loss variable is established on the basis of the first transmission signal and the first reception signal.

In step 507, a second loss variable is established on the basis of the second transmission signal and the second reception signal.

In step 509, a relaxation time constant of the blood picture parameter is ascertained depending on the frequency with a greater loss variable. The glucose concentration in the blood, for example, can then be ascertained depending on the ascertained relaxation time constant.

Figure 6:
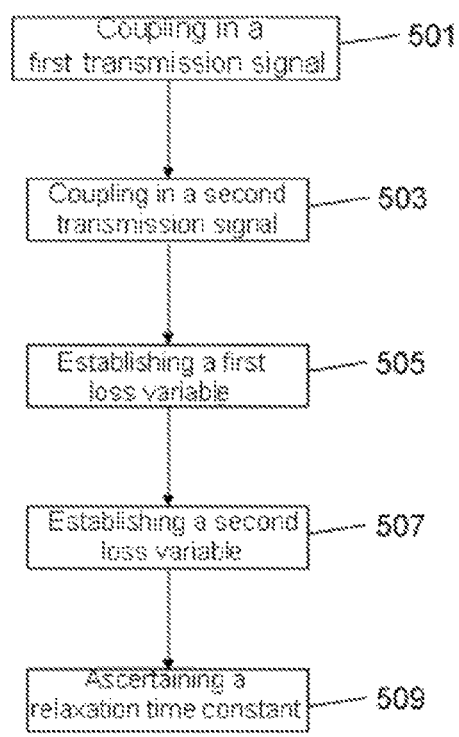
FIG. 6 shows a schematic block diagram of an armband.
Figure 6:
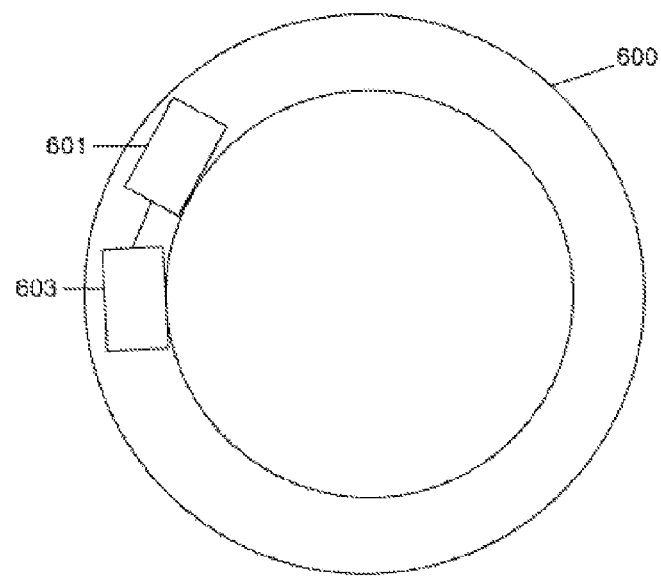

FIG. 6 shows a block diagram of an exemplary embodiment of an armband 600 with a detection device 601 and a setting device 603. The detection device 601 is configured to detect a blood picture parameter of blood in a blood vessel of the arm. An example for the blood picture parameter to be detected is the glucose concentration in the blood.

The setting device 603 is configured to set a predeterminable contact pressure of the armband 600 on the arm. By setting the predetermined contact pressure of the armband 600, the setting device 603 can ensure reproducible detections of the blood picture parameter by the detection device 601. To this end, the setting device 603 is, in particular, configured to set the contact pressure of the armband 600 to the predeterminable contact pressure when the blood picture parameter is being detected by the detection device 601.

In particular, the armband 600 is embodied as an inflatable armband 600. Here, the setting device 603 in particular has an air pump, which is configured to inflate the armband 600 for setting the predetermined contact pressure.

In detail, the detection device 601 comprises electrodes in particular, which are configured to couple at least a radiofrequency signal into the blood vessel. The radiofrequency signal is configured to supply a parameter for detecting the blood picture parameter. An example for such a parameter is formed by the relaxation time constant τ of the blood picture parameter. Here, the setting device 603 is more particularly designed to set the contact pressure of the electrodes on the arm to the predetermined contact pressure.

Furthermore, the setting device 603 can be embodied in such a way that it distributes the contact forces of the armband 600 uniformly on the arm when the blood picture parameter is being detected by the detection device 601. Furthermore, the setting device 603 is preferably configured in such a way that it ensures uniform contact of the armband 600 while the blood picture parameter is being detected by the detection device 601.

Figure 7:
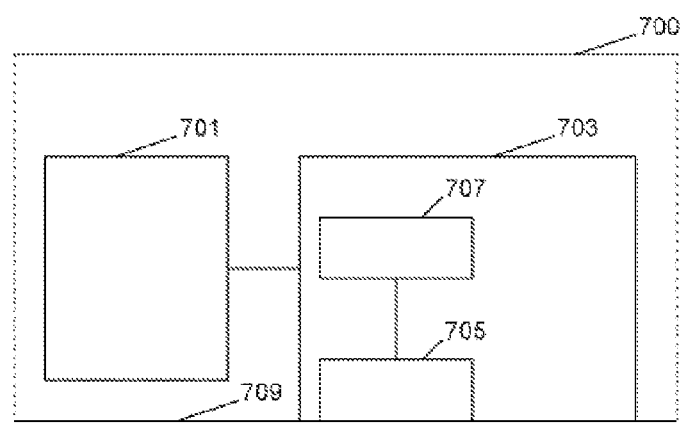
FIG. 7 shows a schematic block diagram of a section of an exemplary embodiment of an armband.

FIG. 7 shows a block diagram of a section of an exemplary embodiment of an armband 700. The armband 700 has a detection device 701 and a setting device 703. The detection device 701 and the setting device 703 are embodied at least like the detection device 601 and the setting device 603 of FIG. 6. Furthermore, the setting device 703 of FIG. 7 has a sensor apparatus 705 and a control apparatus 707. The sensor apparatus 705 is configured to measure a current contact pressure of the armband 700 on the arm. Depending on the measured current contact pressure, the control apparatus 707 sets the predetermined contact pressure on the arm.

Figure 8:
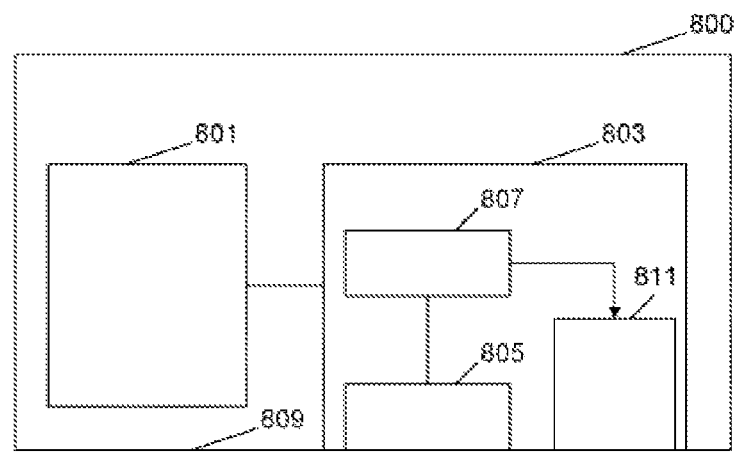
FIG. 8 shows a schematic block diagram of a section of an armband.

FIG. 8 shows a block diagram of a section of a further exemplary embodiment of an armband 800. The armband 800 has a detection device 801 and a setting device 803. The setting device 803 has a sensor apparatus 805, a control apparatus 807 and an air pump 811. The sensor apparatus 805 measures a current contact pressure of the armband 800 on the arm. The control apparatus 807 provides a control signal depending on the measured current contact pressure. By means of the provided control signal, the air pump 811 is controlled for inflating the armband 800.

Figure 9:
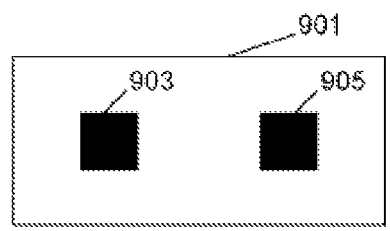
FIG. 9 shows a schematic block diagram of an arrangement of the electrodes of the detection device.

FIG. 9 illustrates a schematic block diagram of an arrangement 900 of the electrodes 903, 905 of the detection device for detecting a blood picture parameter of blood in a blood vessel of the arm.

Without loss of generality, the arrangement 900 only shows two electrodes 903 and 905. In particular, the arrangement 900 is part of the detection device and, for example, embodied as a plate with exemplary dimensions of 5 cm by 2 cm. The electrodes 903, 905 for example have a base area of 5 mm by 5 mm. By way of example, the distance between the electrodes 903, 905 is 1 to 2 cm. This firstly obtains a strong enough transmission and secondly ensures a sufficiently deep penetration depth into the body.

Figure 10:
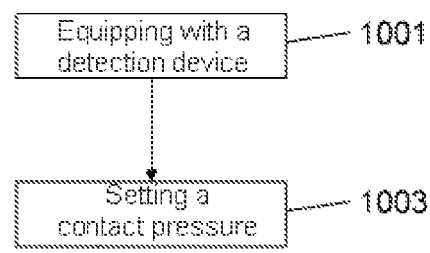
FIG. 10 shows a schematic flowchart of a method for operating an armband.

FIG. 10 shows a schematic flowchart of a method for operating an armband with a detection device.

In step 1001, the armband is equipped with a detection device for detecting a blood picture parameter of blood in a blood vessel of the arm. By way of example, the detection device is configured in accordance with one of the exemplary embodiments of FIG. 6, 7 or 8.

In step 1003, a predetermined contact pressure of the armband on the arm is set. Hence, reproducible detection of the blood picture parameter is ensured by the detection device.

Figure 11:
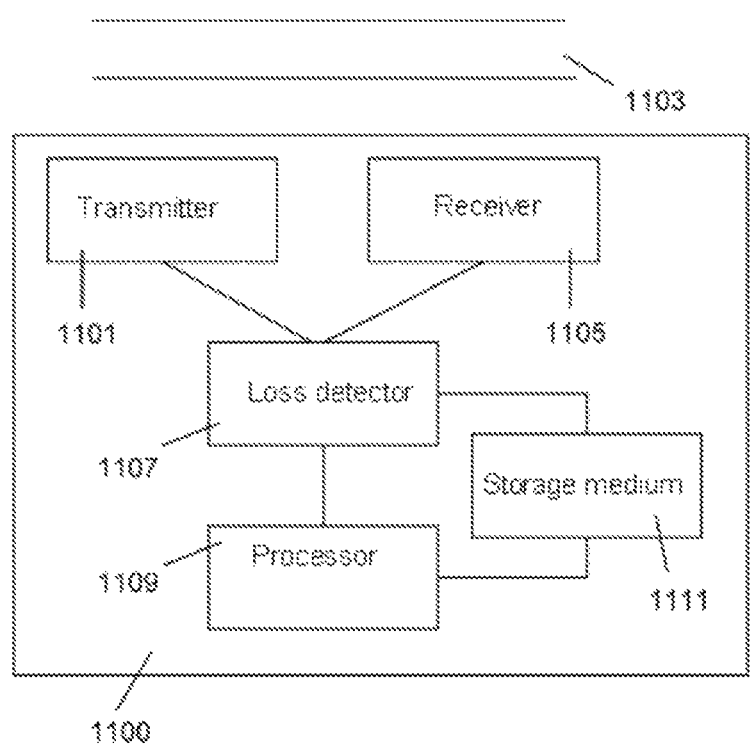
FIG. 11 shows a block diagram of a detection device.

FIG. 11 shows a block diagram of a detection device 1100 for detecting a blood picture parameter such as, for example, a concentration of blood sugar. The detection device 1100 comprises a transmitter 1101, which is configured to couple a first transmission signal with a first frequency and a second transmission signal with a second frequency into the blood vessel 1103 illustrated schematically in FIG. 11. By way of example, together, the first transmission signal and the second transmission signal can result in a broadband signal. The transmitter 1101 can be configured to emit, one after the other, the first transmission signal and the second transmission signal, for example by a frequency sweep. To this end, the transmitter 1101 can have one or more transmission antennas, which can, for example, be embodied as dipole antennas or frame antennas or patch antennas.

The detection device 1100 furthermore comprises a receiver 1105, which is configured to receive a first reception signal at the first frequency and a second reception signal at the second frequency. To this end, the receiver 1105 can have one or more reception antennas.

The detection device 1100 furthermore comprises a loss detector 1107, which, for example, is coupled to the transmitter 1101 and the receiver 1105 and is provided for ascertaining a first loss variable on the basis of the first transmission signal and the first reception signal and also a second loss variable on the basis of the second transmission signal and the second reception signal.

The detection device furthermore comprises a processor 1109, which is coupled to the loss detector 1107 and is provided for ascertaining a first frequency shift of the first loss variable relative to a first reference loss variable and a second frequency shift of the second loss variable relative to a second reference loss variable. The processor 1109 can furthermore be configured to ascertain the blood picture parameter on the basis of the two frequency shifts.

The detection device 1100 can furthermore have a storage medium 1111, which can be accessed by, for example, the processor 1109 and, optionally, the loss detector 1107. By way of example, the first and the second reference loss variable or a plurality of reference loss variables are stored in the storage medium 1111. By way of example, the reference loss variables can be absorptions or absorption lines of a water solution with a blood constituent, for example blood sugar. The loss variables detected on the basis of the frequency shifts can be frequency-shifted absorptions or absorption lines such that the blood picture parameter, such as, for example, a concentration of blood sugar, can be established on the basis of the frequency shifts.

The detection device 1100 illustrated in FIG. 11 uses the discovery that a blood vessel, a layer of skin and fatty tissue surrounding the blood vessel of, for example, a human forearm can be considered to be a dielectric waveguide system. By way of example, if the transmitter 1101 and the receiver 1105, illustrated in FIG. 11, are placed onto the upper layer of skin, the transmitter 1101 can be used to couple e.g. a transverse electric (TE) wave or a transverse magnetic (TM) wave into the dielectric waveguide system formed by a blood vessel, fatty tissue and a layer of skin. Here, the layer of skin and the fatty tissue can be understood to be a thin-film waveguide.

By way of example, if use is made of a microwave measurement head, as can be employed for ascertaining a complex relative permittivity of materials, it is possible thereby to characterize the substance mixture consisting of skin, fatty tissue and veins.

In order to detect a blood picture parameter, it is advantageous to detect substantially only the venous blood. To this end, the transmitter 1101 can be configured to couple the transmission signal in the form of an electromagnetic wave directly into the blood vessel. The transmitter 1101 and the receiver 1105 can each have a plurality of antennas such that, for the purposes of coupling the electromagnetic wave into the blood vessel and decoupling an electromagnetic wave from the blood vessel, it is in each case possible to select that transmission antenna and reception antenna which are connected with the smallest coupling losses.

Figures 12A, 12B, 12C:
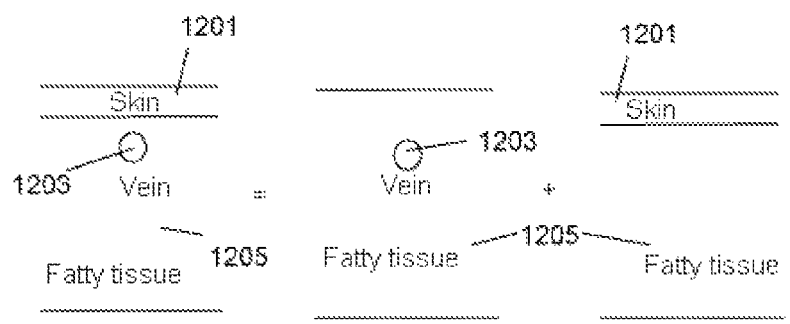
FIG. 12 shows a model of a cross-section of a human forearm.

FIGS. 12A to 12C illustrate a simplified model of a cross-section of a human forearm, e.g. of a wrist, as can be employed, for example, for field simulations or for modeling a dielectric waveguide system. As illustrated in FIG. 12A, the model comprises a layer of skin 1201, a blood vessel 1203 and fatty tissue 1205 surrounding the blood vessel 1203. The model illustrated in FIG. 12A forms a dielectric waveguide system comprising the dielectric waveguide illustrated in FIG. 12B and the electrical thin-film waveguide illustrated in FIG. 12C.

The dielectric waveguide illustrated in FIG. 12B comprises the blood vessel 1203 and the fatty tissue 1205 surrounding the latter. By contrast, the dielectric thin-film waveguide from FIG. 12C comprises the layer of skin 1201 and the fatty tissue 1205. A different dispersive, i.e. frequency dependent, behavior of the respective complex relative permittivity can be attached in each case to the layer of skin 1201, to the fatty tissue 1205 and to the blood vessel 1203. Here, the blood vessel 1203 lying at the top is interpreted as a dielectric waveguide, in which, depending on the frequency, different modes or wave types, for example a TE wave, a TM wave, a TEM wave or an HE wave, are able to propagate. Added to the waveguide mechanism in the dielectric waveguide, there is an additional waveguide mechanism in the form of the thin-film waveguide illustrated in FIG. 12C, which is formed by the upper layer of skin 1201.

A transmission antenna of the transmitter 1101 and a reception antenna of the receiver 1105 can preferably be configured in such a way that they couple microwave power into the blood vessel 1203 in a dedicated fashion and decouple said microwave power again after, for example, a few centimeters. Here, the blood vessel 1203 serves as a measurement length and should therefore be considered as a distributed element and no longer as a concentrated element. The measurement of the loss variables is preferably carried out on the basis of a two-port measurement. Here, particularly when coupling the detection device to a wrist, primary modes can be excited in the dielectric waveguide in accordance with FIG. 12B such that an excitation of thin-film waveguide modes in the thin-film waveguide in accordance with FIG. 12C is avoided, as a result of which the blood picture parameter can be detected more accurately.

In order to excite primary modes in the dielectric waveguide system, it is possible to take into account that, depending on the selected frequency of a transmission signal, different modes can be dominant. It is preferable for mode types, which have a concentration of the fields in the vein 1203, to be preferred over those modes in which the fields are concentrated in the layer of skin 1201. What is shown on the basis of the dielectric properties of the dielectric waveguide illustrated in FIG. 12B is that for certain types of modes longitudinal components $E_{longitudinal}$, $H_{longitudinal}$ are stronger in the propagation direction, i.e. in the direction of a vein extent, than the transverse components $E_{transverse}$, $H_{transverse}$, i.e. transverse to the vein extent. Therefore those modes which enable maximum coupling of the microwave power into the blood vessel 1203 are preferably excited in the frequency range to be detected.

FIGS. 13A to 13D illustrate some antennas in an exemplary fashion, which antennas can be used as transmission antennas, i.e. excitation means, or else as reception antennas.

Figure 13A:
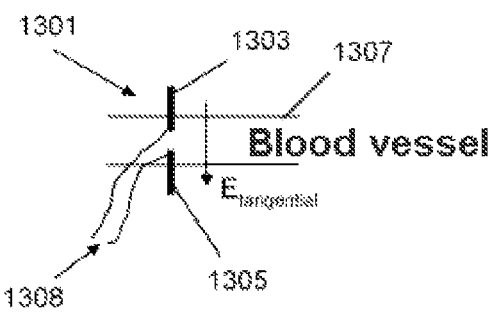
FIGS. 13A-13D show antennas.

The antenna 1301 illustrated in FIG. 13A is configured as an electric dipole with a first antenna section 1303 and a second antenna section 1305. The antenna sections 1303 and 1305 are distanced from one another and are arranged, for example, transversely with respect to the extent of a blood vessel 1307. The antenna 1301 can be excited by supply lines 1308. An electric dipole arranged in this manner can, for example, generate an electric field $E_{tangential}$, which points across the extent of the blood vessel or across the blood flow direction.

Figure 13B:
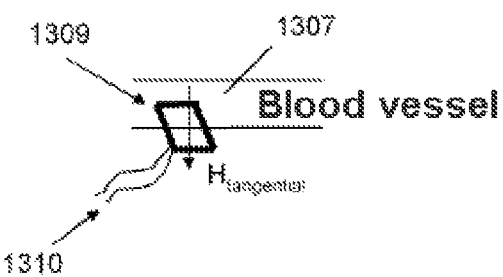

FIG. 13B illustrates an antenna 1309, which can be a frame antenna. By way of example, the frame antenna can have a quadrilateral or round shape. In the arrangement of the frame antenna 1309 with respect to the blood vessel 1307 illustrated in FIG. 13B, e.g. a magnetic field $H_{tangential}$ is excited, which points across the extent of the blood vessel 1307 or across the blood flow direction. The antenna 1309 can be excited by supply lines 1310.

Figure 13C:
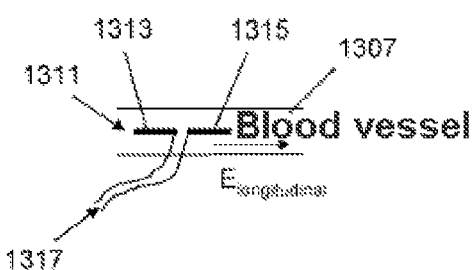

FIG. 13C illustrates an antenna 1311, which forms an electric dipole with a first antenna section 1313 and a second antenna section 1315. The antenna sections 1313 and 1315 are distanced from one another and are excited by means of the supply lines 1317 illustrated in FIG. 13C. The electric dipole formed by the antenna 1311 is arranged in such a way with respect to the extent of the blood vessel 1307 that the sections 1313 and 1315 are arranged parallel to the extent of the blood vessel 1307. As a result of this, an electric field with the field component $E_{longitudinal}$, which electric field points in the direction of the extent of the blood vessel, is excited.

Figure 13D:
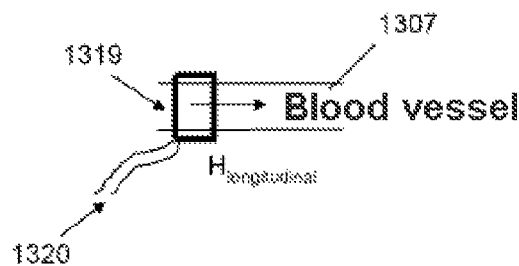

FIG. 13D shows a frame antenna 1319, which can, for example, be formed in the form of a quadrilateral or round frame, which forms a loop antenna, for example as a patch antenna. The frame antenna 1319 is excited by means of supply lines 1320 and is, as illustrated in FIG. 13D, arranged in such a way with respect to the extent of the blood vessel 1307 or with respect to the blood flow direction that the magnetic field has a component $H_{longitudinal}$ pointing in the direction of the extent of the blood vessel 1307.

By way of example, the frequency range to be measured in each case conforms to which spectral lines, i.e. which absorption lines, should be detected. By way of example, it is possible to observe the characteristic absorption lines of a substance or else an effect which a specific blood constituent has on the absorption lines of water or of a water solution with a concentration of the blood constituent.

The antennas illustrated in FIGS. 13A to 13D are either electric dipoles or magnetic frame antennas. Moreover, use can also be made of patch antennas. Electric dipoles dominantly produce an electric field along the axis of the electric dipole. This axis can either, as illustrated in FIG. 13A, be aligned tangentially with respect to the blood vessel 1307 or the blood flow direction or, as illustrated in FIG. 13C, be aligned in the direction of the blood vessel 1307 or in the blood flow direction. If it is primarily a magnetic field that should be generated, a frame antenna can be used as excitation means. If a surface vector on the surface spanned by the frame forming the frame antenna is aligned across the blood vessel 1307 or across the blood flow direction, the magnetic field is also aligned across the blood vessel 1307, as illustrated in FIG. 13B. By contrast, if the surface vector points in the direction of the blood vessel 1307, the magnetic field is also aligned in the direction of the blood vessel 1307, as is illustrated in, for example, FIG. 13B. The selection of an excitation means illustrated in FIGS. 13A to 13D then results in, for example, the dominant excited mode or wave type.

Figure 14A:
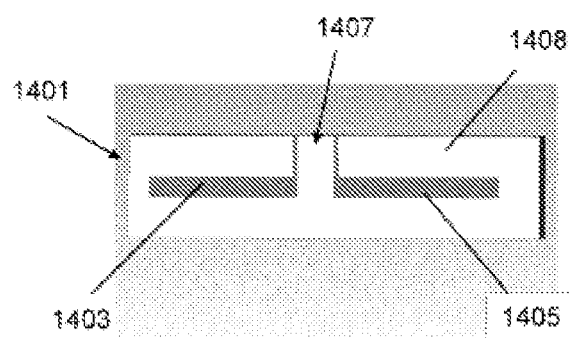
FIG. 14 shows an electric dipole antenna.
FIG. 14B shows an excitation arrangement.

FIG. 14A shows an electric dipole antenna 1401, which can be used as a transmission antenna or as a reception antenna. The electric dipole antenna 1401 comprises dipole antenna sections 1403 and 1405, which are arranged in or on a substrate 1408 and can be excited by means of supply lines 1407. The dipole antenna 1401 can be used as a transmission antenna or as a reception antenna.

Figure 14B:
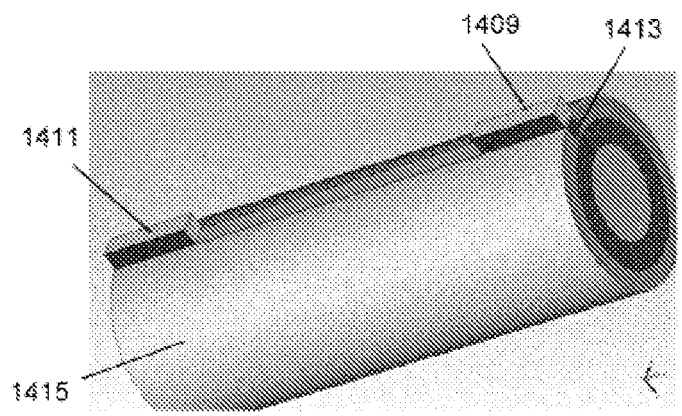

FIG. 14B shows an excitation arrangement of a transmission antenna 1409 of a transmitter and of a reception antenna 1411 of a receiver in the direction of an extent of a blood vessel 1413 below a layer of skin 1415. The transmission antenna 1409 and the reception antenna 1411 are, for example, electric dipole antennas in accordance with FIG. 14A. In the arrangement illustrated in FIG. 14B, an electric field with a field component in the direction of the extent of the blood vessel 1413, or in the blood flow direction, is generated.

Figure 15A:
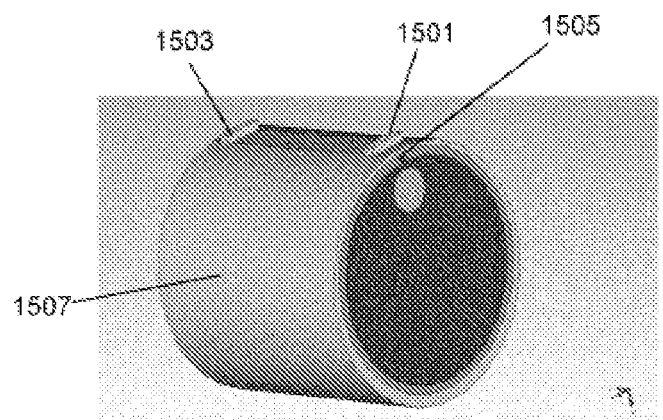
FIGS. 15A, 15B show excitation arrangements.
Figure 15B:
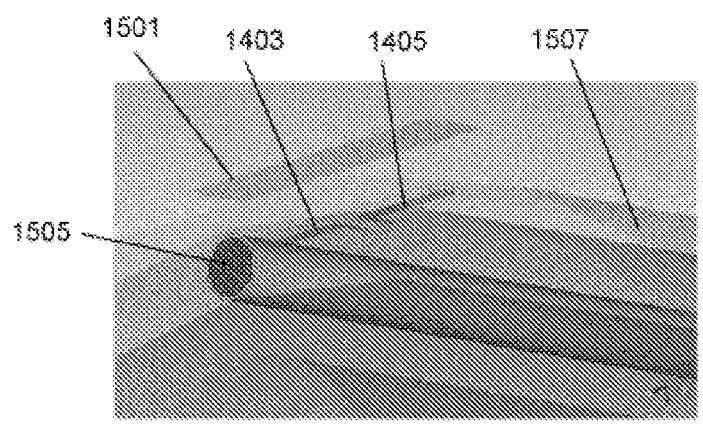

FIG. 15A shows an excitation arrangement comprising a transmission antenna 1501 of a transmitter and a reception antenna 1503 of a receiver, across the direction of extent of a blood vessel 1505, i.e. across the blood flow direction, which lies under a layer of skin 1507. The transmission antenna 1501 and the reception antenna 1503 can each be formed by e.g. the electric dipole antenna illustrated in FIG. 14A. In FIG. 15B, the arrangement of the dipole antenna sections 1403 and 1405 is illustrated in more detail in respect of the blood flow direction.

Figure 16A:
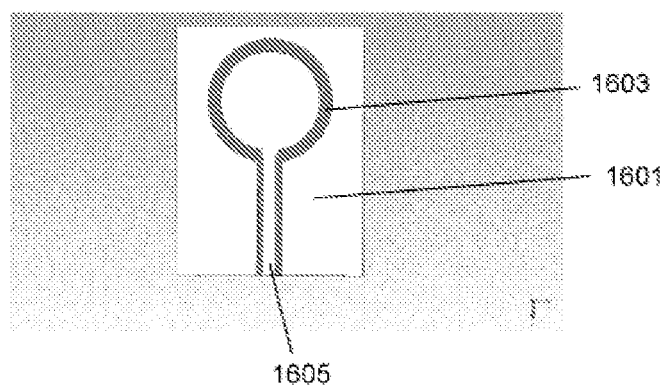
FIG. 16A shows a loop antenna.

FIG. 16A shows a loop antenna 1601 with a circular frame 1603 and supply lines 1605 for exciting the circular frame 1603. The loop antenna 1601 can, for example, be used as a transmission antenna or as a reception antenna. The circular frame 1603 and the supply lines 1605 can be arranged in or on a substrate.

Figure 16B:
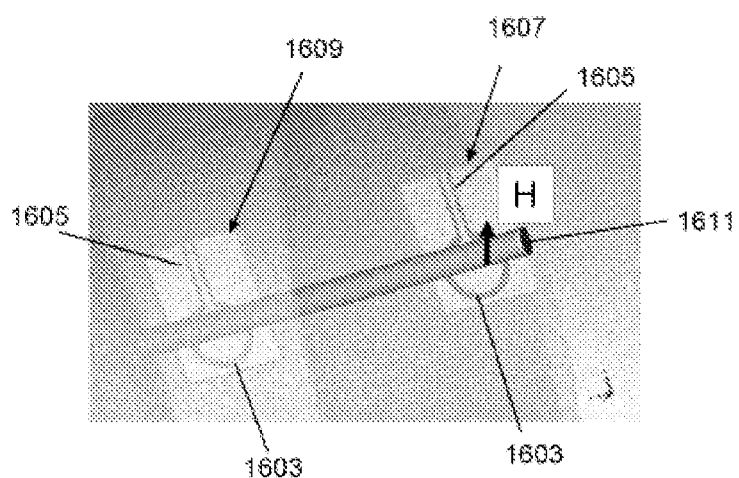
FIG. 16B shows an excitation arrangement.

FIG. 16B shows an excitation arrangement with a transmission antenna 1607 of a transmitter and a reception antenna 1609 of a receiver, which can be formed as loop antennas as per FIG. 16A. By way of example, the loop antennas 1607, 1609 are arranged in such a way that the circular frames 1603 are arranged above a blood vessel 1611, with the supply lines 1605 pointing across the extent of the blood vessel 1611, i.e. across the blood flow direction. As a result of this, a magnetic field H with a component of the magnetic field pointing across the extent of the blood vessel 1611 is generated on the transmitter side.

Figure 17:
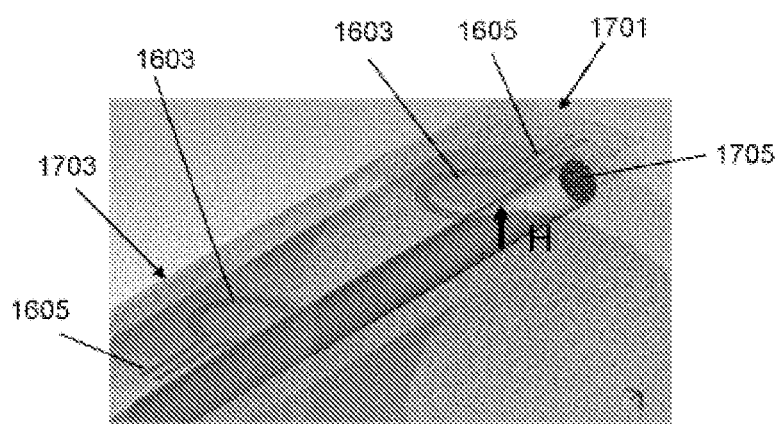
FIG. 17 shows an excitation arrangement.

FIG. 17 shows an excitation arrangement of a transmission antenna 1701 of a transmitter and a reception antenna 1703 of a receiver, with respect to a blood vessel 1705. By way of example, the transmission antenna 1701 and the reception antenna 1703 can be loop antennas with that shape illustrated in FIG. 16A. By way of example, they are arranged in such a way that the circular frames 1603 are respectively arranged above the blood vessel 1705 and that the supply lines 1605 extend pointing away from one another, parallel to the extent of the blood vessel 1705. As a result of this, a field component H pointing perpendicular to the extent of the blood vessel 1705 is generated, which field component points in the direction of a normal of the surface spanned by the circular frame 1603.

Figure 18:
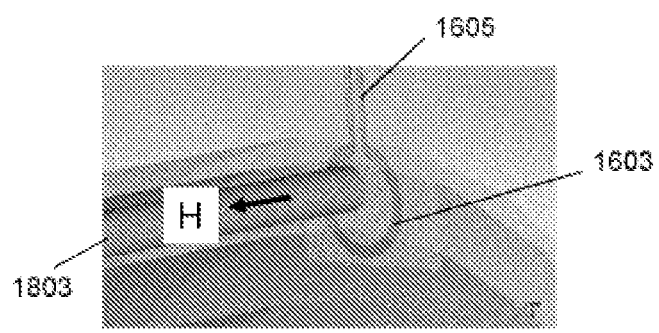
FIG. 18 shows an excitation arrangement.

FIG. 18 shows an excitation arrangement with a transmission antenna 1801 of a transmitter, which, for example, has the shape of a loop antenna illustrated in FIG. 16A. By way of example, the transmission antenna 1801 is arranged in such a way with respect to a blood vessel 1803 that a normal of the surface spanned by the frame 1603 points in the direction of the extent of the blood vessel 1803. By way of example, such an arrangement can be realized at a bend in the blood vessel 1803. As a result of this, a magnetic field component H pointing in the direction of the extent of the blood vessel 1803 is generated.

Figure 19:
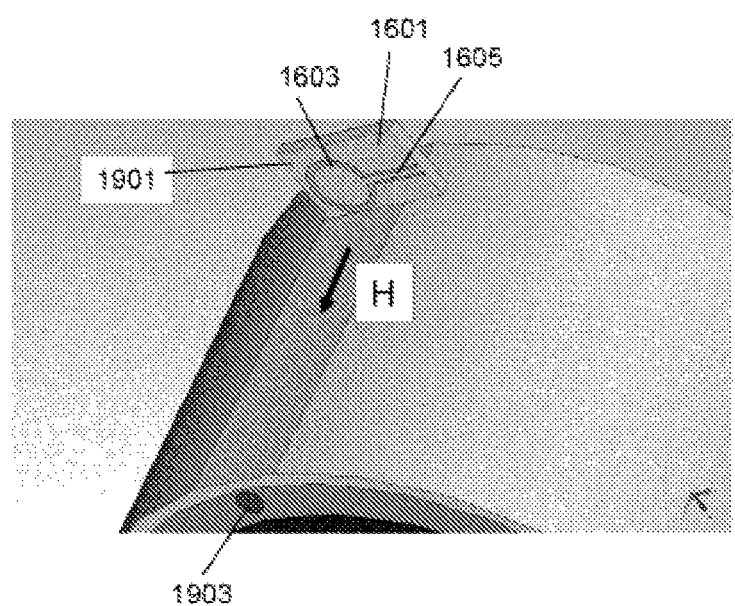
FIG. 19 shows an excitation arrangement.

FIG. 19 shows an excitation arrangement with a transmission antenna 1601, which, for example, is a loop antenna with the shape illustrated in FIG. 16A and can be arranged in a substrate 1901, for example a polymer substrate. The transmission antenna 1601 is arranged above a blood vessel 1903 in such a way that a normal of the surface spanned by the circular frame 1603 points in the direction of the extent of the blood vessel 1903. As a result of this, a magnetic field is generated with a field component H pointing in the direction of the extent of the blood vessel 1903, i.e. in the blood flow direction.

Figure 20:
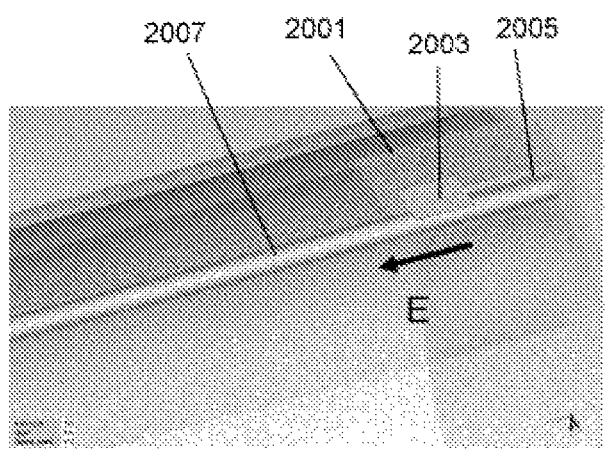
FIG. 20 shows an excitation arrangement.

FIG. 20 shows an excitation arrangement with a transmission antenna 2001, which can be a patch antenna with a patch antenna surface 2003 and supply lines 2005. The patch antenna surface 2003 is, for example, arranged above a blood vessel 2007, as a result of which an electric field is generated with an electric field component E pointing in the direction of an extent of the blood vessel 2007, i.e. in the blood flow direction.

In accordance with one embodiment, the loss detector 1107 is configured to carry out e.g. a scalar or a vector measurement or a power measurement. In order to ascertain the loss variables, a simple spectroscopic measurement can be carried out, in which the absolute value of the measurement parameter S21 is detected.

Figure 21:
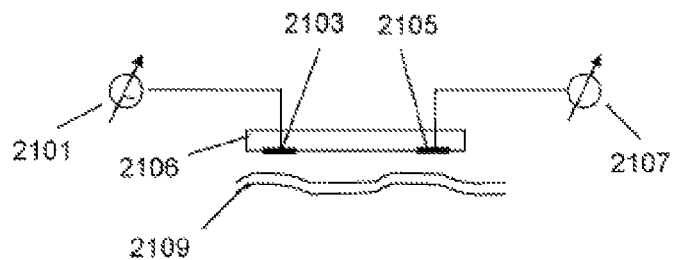
FIG. 21 shows a block diagram of a detection device.

By way of example, $|S_{21}|$ can be measured by means of the detection device illustrated in FIG. 21. The detection device comprises a transmitter with a transmission signal generator 2101, which can be a tunable oscillator. An output of the transmission signal generator 2101 is connected to a transmission antenna 2103. The detection device furthermore comprises a receiver with a reception antenna 2105, the output of which is connected to a loss detector 2107. By way of example, the loss detector can comprise a power detector. As illustrated in FIG. 21, the transmission antenna 2103 and the reception antenna 2105 are arranged above a blood vessel 2109. The transmitter can correspond to features of the transmitter 1101, the receiver can correspond to features of the receiver 1105 and the loss detector 2107 can correspond to features of the loss detector 1107.

However, the accuracy when ascertaining the loss variables, i.e. the losses in the waveguide, can be increased further by a further measurement of an absolute value of the measurement parameter S11. By way of example, the loss variables can be ascertained on the basis of the following formula:

$$P_{loss}=1-|S_{11}|^2-|S_{21}|^2,$$

where $P_{loss}$ denotes the respective loss variable and where $S_{11}$ denotes the input reflection factor and $S_{21}$ denotes the forward transmission factor.

Figure 22:
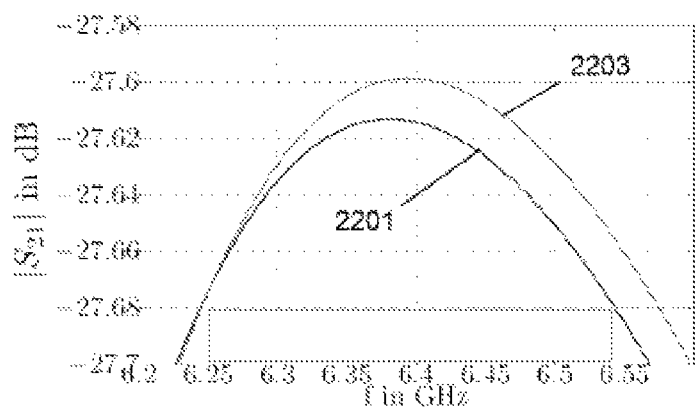
FIG. 22 shows a frequency shift of an absorption maximum.

In order to detect the blood picture parameter, for example a concentration of blood sugar, frequency shifts of the absorption lines of a water solution with sugar can, for example, be examined. By way of example, FIG. 22 shows a frequency shift of an absorption maximum 2201 at a first blood sugar concentration compared to a frequency shift of an absorption maximum 2203 at a second blood sugar concentration, which is higher than the first blood sugar concentration. Here, a transmission around 6 GHz was detected in an exemplary fashion as loss variable.

The frequency shift of the absorption maximum can be considered to be a measure for a blood picture parameter, for example for a blood sugar level. By observing frequency shifts in a number of absorptions of a water solution with sugar, the measurement reliability can be increased still further.

Figures 23, 24:
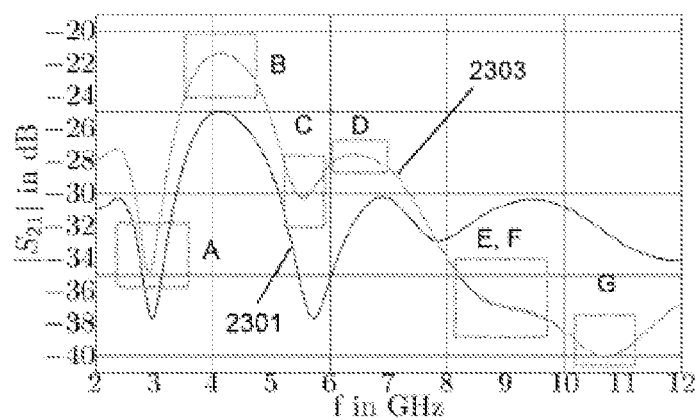
FIG. 23 shows a transmission behavior.
FIG. 24 shows frequency shifts.

FIG. 23 shows, in an exemplary fashion, a broadband transmission behavior of venous blood in a wrist. Here, the profiles 2301 and 2303 clarify different frequency positions of absorption lines at different blood sugar concentrations. In order to detect the blood picture parameter, such as, for example, the concentration of the blood sugar, it is possible, for example, to detect frequency shifts of the absorptions A, B, C, D, E, F and G in a targeted manner. Thus, it is possible, for example, to observe a shift in the direction of higher or lower frequencies depending on blood sugar level, for example in a frequency range between 2 GHz and 12 GHz, for each frequency of an absorption maximum and/or an absorption minimum.

FIG. 24 shows, in an exemplary fashion, frequency shifts of the absorptions A, B, C, D, E, F and G illustrated in FIG. 23 for a blood vessel with a diameter of 6 mm and for a blood vessel with a diameter of 3.4 mm. It is possible to identify that the absorptions for a sugar level variation can have frequency shifts in both positive and negative directions. Detecting a plurality of absorptions or absorption lines therefore makes it possible to detect a blood picture parameter, for example the blood sugar level, more accurately.

Figure 25:
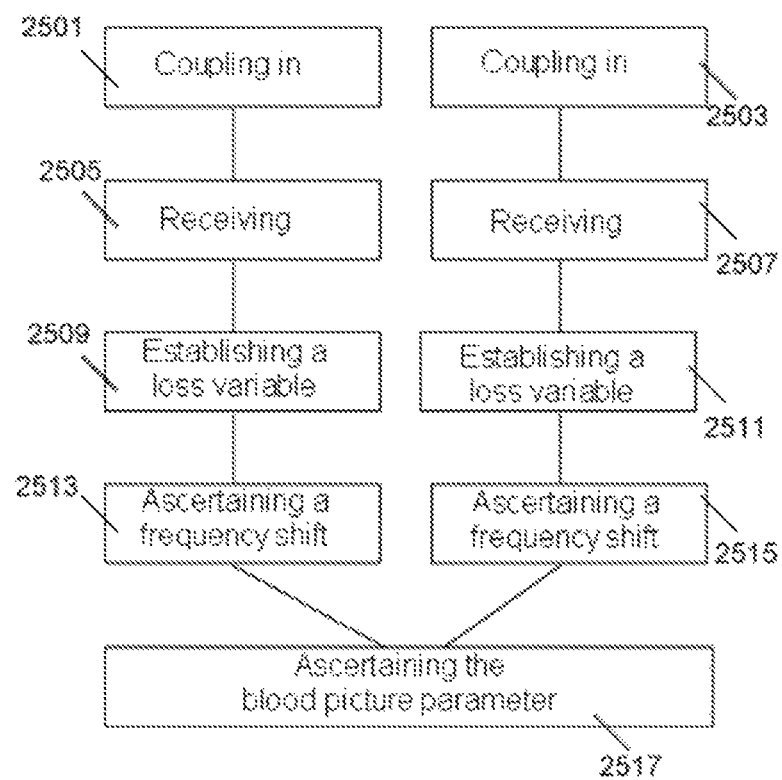
FIG. 25 shows a diagram of a method for detecting a blood picture parameter.

FIG. 25 shows a diagram of a method for detecting a blood picture parameter of blood in a blood vessel. The method comprises a first transmission signal with a first frequency being coupled 2501 into the blood vessel, a second transmission signal with a second frequency being coupled 2503 into the blood vessel, a first reception signal being received 2505 at the first frequency, a second reception signal being received 2507 at the second frequency, a first loss variable being established 2509 on the basis of the first transmission signal and the first reception signal at the first frequency, a second loss variable being established 2511 on the basis of the second transmission signal and the second reception signal at the second frequency, a first frequency shift of the first loss variable being ascertained 2513 relative to a first reference loss variable, a second frequency shift of the second loss variable being ascertained 2515 relative to a second reference loss variable and the blood picture parameter being ascertained 2517 on the basis of the first frequency shift and the second frequency shift.

By way of example, the method illustrated in FIG. 25 can be executed by the detection device illustrated in FIG. 11.

Figure 26:
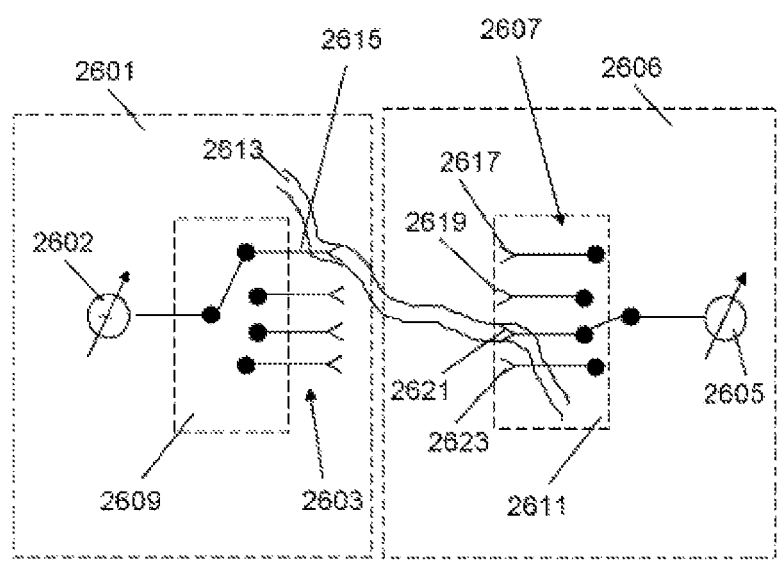
FIG. 26 shows a block diagram of a detection device.

FIG. 26 shows a detection device with a transmitter 2601, which detection device, for example, comprises a tunable oscillator 2602 and a plurality of transmission antennas 2603. The detection device furthermore comprises a loss detector 2605, which can, for example, have a power detector. Furthermore, provision is made for a receiver 2606 with a plurality of reception antennas 2607.

One output of the tunable oscillator 2602 can be connected to each antenna input, for example in succession or in any sequence, in a switchable manner, for example by means of a switching matrix 2609. Analogously to this, each output of a reception antenna of the plurality of reception antennas 2607 can be connected to the loss detector 2605 by means of a switching matrix 2611.

By way of example, the switching matrix 2611 and the switching matrix 2609 can be used to select that pair comprising a transmission antenna and a reception antenna which enables optimum coupling of a microwave signal into a blood vessel 2613 illustrated schematically in FIG. 26. The switching matrices 2609 and 2611 are used to select the antenna pairs in succession, starting with, for example, a first transmission antenna 2615 by means of which a transmission signal is emitted. The switching matrices 2609, 2611 can have switches, for example transistor switches.

On the reception side, the switching matrix 2611 is used to select the reception antennas in succession, starting with, for example, the reception antenna 2617 for receiving a corresponding reception signal, with a loss variable being detected on the basis of the transmission signal and the reception signal. In the next step, the reception antenna 2619 is for example selected, with a loss variable once again being detected by means of the loss detector on the basis of the transmission signal and a reception signal received by the reception antenna 2619. After this, for example, the reception antenna 2621 is selected, with a further loss variable being detected on the basis of the transmission signal and a reception signal. In the next step, the reception antenna 2623 is selected and a further loss variable is ascertained on the basis of the transmission signal and a reception signal received by the reception antenna 2623. In the next step, the switching matrix 2609 can, for example, select a further transmission antenna, wherein the aforementioned steps can be repeated. By a comparison of the established loss variables, the smallest loss variable, for example, is selected. In the example illustrated in FIG. 26, it is to be expected, for example, that the detection configuration with the transmission antenna 2615 and the reception antenna 2621 is afflicted with the smallest coupling-in losses because the antennas 2615, 2621 lie directly above the blood vessel and therefore enable a signal to be coupled into the blood vessel 2613 in an optimum manner. By way of example, the selected detection configuration can be used for detecting a blood picture parameter. The above-described selection steps can be carried out in any sequence. Thus, for example, all or some of the reception antennas 2607 can be tested for the transmission antenna 2615.

The transmission antennas 2603 or the reception antennas 2607 can differ in respect of their location and/or in respect of their field component which should be excited in a dominant fashion. Here, the switching matrices 2609 and 2611 ensure that the optimal excitation type, for example a loop antenna, an electric dipole antenna, a patch antenna, or excitation location can be selected for the respectively selected frequency.

By way of example, the detection device illustrated in FIG. 26 can be integrated in an inflatable armband. Between the detections of the loss variables, which can, for example, take place by measuring the control parameters, air can be allowed to escape from the armband such that the skin is aerated and no sweat is formed. A time interval between the measurements can be variable in this case. By way of example, the measurements can be carried out at intervals of 10 minutes. However, depending on requirement, more frequent measurements can be carried out, wherein the frequency of the measurements can be ascertained, for example, by the times when the meals are taken.

Since the transmission or reception antennas, which lie on the skin and can respectively be formed by an electrode plate, can slip, particularly in the pauses between the measurements, the selection of a plurality of excitation means illustrated in FIG. 26 can ensure that an excitation means which lies over the blood vessel 2613 is selected. Hence that excitation means which enables a maximum of coupling microwave energy into the blood vessel 2613 can be selected by means of the respective switching matrix 2609 and 2611.

The invention claimed is:

1. A detection device for detecting at least one blood picture parameter of a blood constituent of blood in a blood vessel, comprising:
   a transmitter mode exciter positioned proximal to a first end of a segment of the blood vessel, wherein the transmitter mode exciter is a means for coupling a first transmission signal with a first frequency and a second transmission signal with a second frequency into the blood vessel such that the first and second transmission signals propagate within the segment of the blood vessel as a waveguide;
   a receiver mode exciter positioned proximal to a second end of the segment of the blood vessel at a distance from the transmitter along the length of the segment of the blood vessel parallel to a blood flow direction, wherein the receiver mode exciter is a means for receiving a first reception signal at the first frequency and a second reception signal at the second frequency from the segment of the blood vessel at the second end of the segment of the blood vessel;
   a loss detector configured to:
      establish a first loss variable on the basis of the first transmission signal and the first reception signal, and establish a second loss variable on the basis of the second transmission signal and the second reception signal; and
   a processor configured to ascertain a relaxation time constant ($\tau$) of the blood constituent depending on the frequency with the greater loss variable and to establish the at least one blood picture parameter based on the ascertained relaxation time constant ($\tau$).

2. The detection device as claimed in claim 1, wherein the processor is configured to establish the at least one blood picture parameter depending on the ascertained relaxation time constant ($\tau$) by a predetermined relationship between the concentration of the blood picture parameter and the relaxation time constant ($\tau$).

3. The detection device as claimed in claim 1, wherein the at least one blood picture parameter comprises a glucose concentration in the blood, a lactate concentration in the blood, or an oxygen concentration in the blood.

4. The detection device as claimed in claim 1, wherein the loss detector is configured to ascertain the first loss variable and the second loss variable by a two-port measurement.

5. The detection device as claimed in claim 1, wherein the loss detector comprises a network analyzer or a power detector.

6. The detection device as claimed in claim 1, wherein the loss detector is configured to ascertain in each case a forward transmission factor $S_{21}$ and an input reflection factor $S_{11}$ to ascertain the first loss variable and the second loss variable.

7. The detection device as claimed in claim 6, wherein the loss detector is configured to ascertain in each case the first loss variable and the second loss variable on the basis of the following formula:

$$P_{loss} = 1 - |S_{11}|^2 - |S_{21}|^2,$$

where $P_{loss}$ denotes the respective loss variable, and where $S_{11}$ denotes the input reflection factor and $S_{21}$ denotes the forward transmission factor.

8. The detection device as claimed in claim 1, wherein the processor is configured to ascertain the relaxation time constant ($\tau$) on the basis of the following formula:

$$\tau = \frac{1}{2\pi f_A}$$

where $f_A$ denotes the frequency at which the established loss variable is greater.

9. The detection device as claimed in claim 1, wherein the loss detector is configured to establish the complex relative permittivity at the respective frequency for ascertaining the respective loss variable.

10. The detection device as claimed in claim 1, wherein the processor is configured to ascertain the frequency at which the imaginary part of the complex relative permittivity ($\in''$) is at a maximum and to establish the relaxation time constant depending on the ascertained frequency.

11. The detection device as claimed in claim 1, wherein the transmitter mode exciter comprises at least one transmission antenna, and wherein the receiver mode exciter comprises at least one reception antenna.

12. The detection device as claimed in claim 1, wherein the transmitter mode exciter is configured to couple the first transmission signal or the second transmission signal into the blood vessel as a transverse electric wave or as a transverse magnetic wave.

13. The detection device as claimed in claim 1, wherein the transmitter mode exciter is configured to couple the first transmission signal and the second transmission signal into the blood vessel successively or simultaneously.

14. A method for detecting a blood picture parameter of a blood constituent of blood in a blood vessel, comprising the following steps:
- positioning a transmitter mode exciter at a first location proximal to a first end of a segment of the blood vessel, wherein the transmitter mode exciter is a means for coupling a first transmission signal with a first frequency and a second transmission signal with a second frequency into the blood vessel such that the first and second transmission signals propagate within the segment of the blood vessel as a waveguide;
- positioning a receiver mode exciter at a second location that is proximal to a second end of the segment of the blood vessel and is separated by a distance along the length of the segment of the blood vessel parallel to a blood flow direction from the first location, wherein the receiver mode exciter is a means for receiving a first reception signal at the first frequency and a second reception signal at the second frequency from the segment of the blood vessel at the second end of the segment of the blood vessel;
- establishing a first loss variable on the basis of the first transmission signal and the first reception signal;
- establishing a second loss variable on the basis of the second transmission signal and the second reception signal;
- ascertaining a relaxation time constant of the blood constituent depending on the frequency with a greater loss variable; and
- establishing the blood picture parameter based on the ascertained relaxation time constant.

15. The detection device as claimed in claim 11, wherein the transmission antenna is a dipole antenna or a frame antenna.

16. The detection device as claimed in claim 11, wherein the reception antenna is a dipole antenna, a frame antenna, or a patch antenna.

17. The detection device as claimed in claim 12, wherein the transmitter mode exciter is configured to couple the first transmission signal or the second transmission signal into the blood vessel as a transverse electric wave or as a transverse magnetic wave longitudinally or transversely with respect to the blood flow direction.

18. The detection device as claimed in claim 13, wherein the transmitter mode exciter is configured to couple the first transmission signal and the second transmission signal into the blood vessel successively by a tunable oscillator or simultaneously.

19. The detection device as claimed in claim 13, wherein the transmitter mode exciter is configured to couple the first transmission signal and the second transmission signal into the blood vessel simultaneously by a broadband signal comprising the first transmission signal and the second transmission signal.

* * * * *